(12) United States Patent
Fortin

(10) Patent No.: US 7,029,472 B1
(45) Date of Patent: Apr. 18, 2006

(54) DISTRACTION DEVICE FOR THE BONES OF CHILDREN

(76) Inventor: Frédéric Fortin, 36 Allée des Passerines, Pessac (FR) F-33600

( * ) Notice: Subject to any disclaimer, the term of this patent is extended or adjusted under 35 U.S.C. 154(b) by 0 days.

(21) Appl. No.: 09/979,974

(22) PCT Filed: May 26, 2000

(86) PCT No.: PCT/FR00/01427

§ 371 (c)(1),
(2), (4) Date: Nov. 4, 2002

(87) PCT Pub. No.: WO00/72768

PCT Pub. Date: Dec. 7, 2000

(30) Foreign Application Priority Data

Jun. 1, 1999 (FR) .................................. 99 07034

(51) Int. Cl.
*A61B 17/68* (2006.01)
(52) U.S. Cl. .......................... 606/60; 606/57; 606/105
(58) Field of Classification Search ............ 606/53–54, 606/55, 57–58, 60–61, 63, 69–71, 105, 213, 606/215, 218
See application file for complete search history.

(56) References Cited

U.S. PATENT DOCUMENTS

| 3,900,025 | A | * | 8/1975 | Barnes, Jr. .................. 606/71 |
| 4,386,603 | A | | 6/1983 | Mayfield |
| 4,611,582 | A | | 9/1986 | Duff |
| 4,658,809 | A | | 4/1987 | Ulrich et al. |
| 4,747,394 | A | * | 5/1988 | Watanabe .................. 600/232 |
| 4,931,055 | A | | 6/1990 | Bumpus et al. |
| 5,129,903 | A | * | 7/1992 | Luhr et al. .................. 606/71 |
| 5,700,263 | A | * | 12/1997 | Schendel .................... 606/57 |
| 5,885,283 | A | * | 3/1999 | Gittleman ................... 606/57 |

FOREIGN PATENT DOCUMENTS

DE  24 37 752 A  2/1976

* cited by examiner

*Primary Examiner*—David O. Reip
(74) *Attorney, Agent, or Firm*—Young & Thompson

(57) ABSTRACT

A distraction device enabling management of the evolving deformation of the trunk of a child during growth. The device is easy to implant on account of its compact shape and includes two rods which can be bent and deformed on the ends thereof and which are mounted on a central adjusting member which is provided with a small hole for engaging a small tool that is designed to adjust the distance separating the elements for attachment to the bone. The inventive device can be locked in a position which is determined by the tightening of two screws which are disposed on the adjusting device.

20 Claims, 5 Drawing Sheets

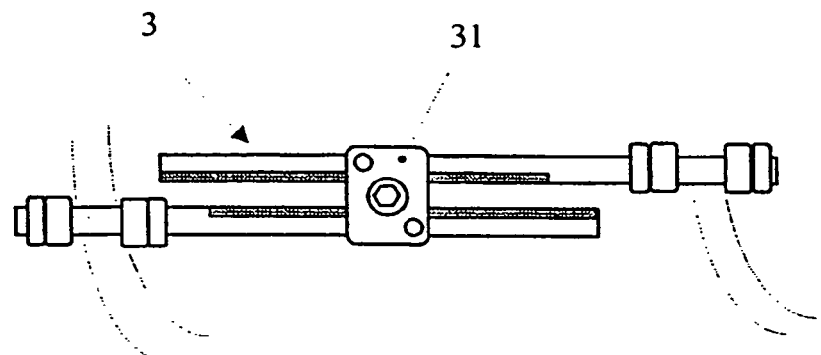
fig.9
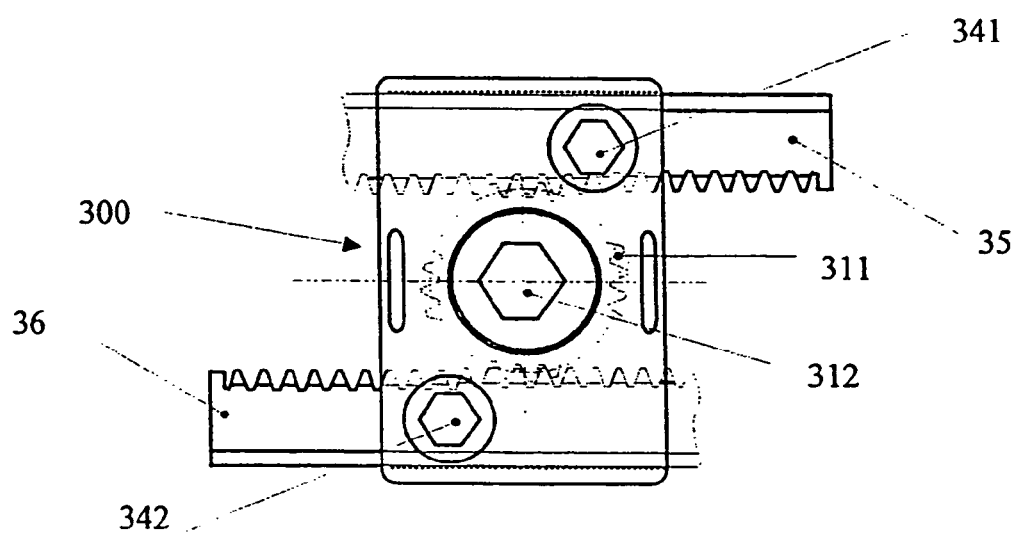
fig.10
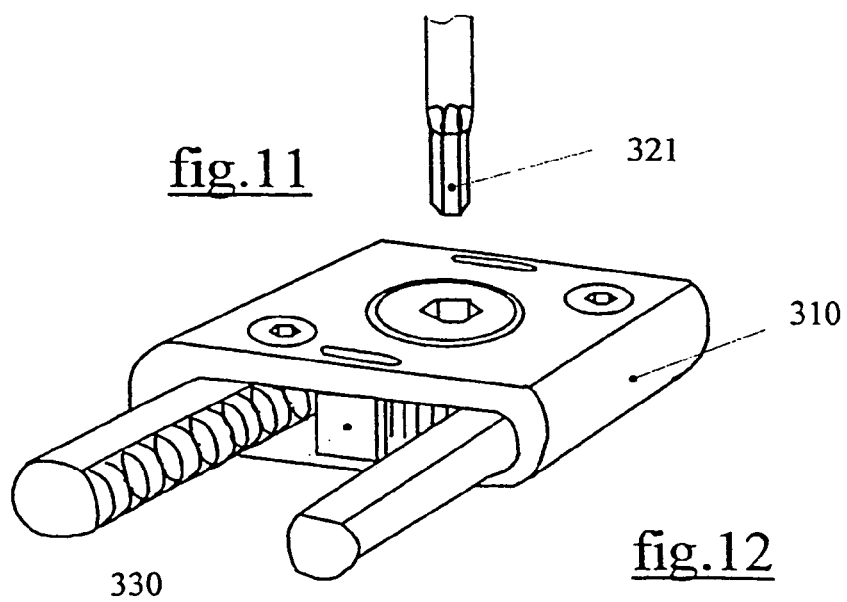
fig.11
fig.12

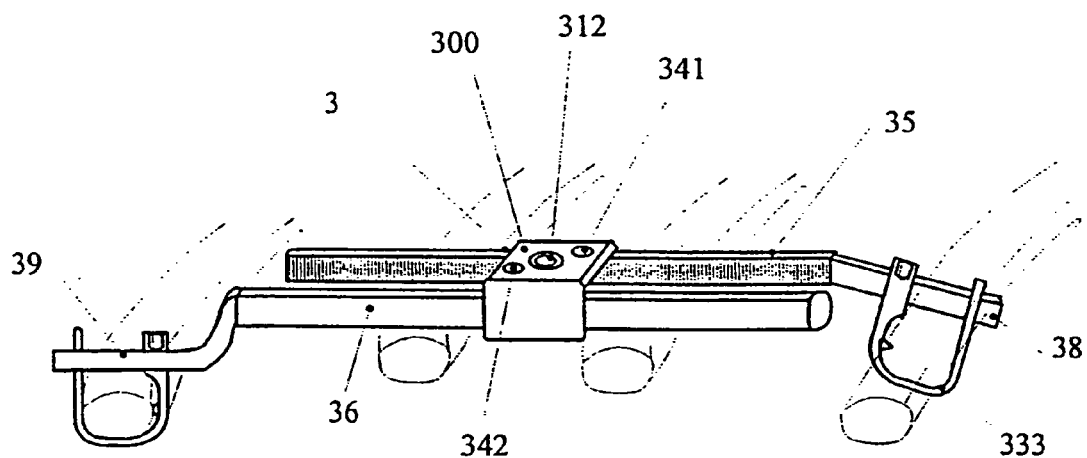
fig.14
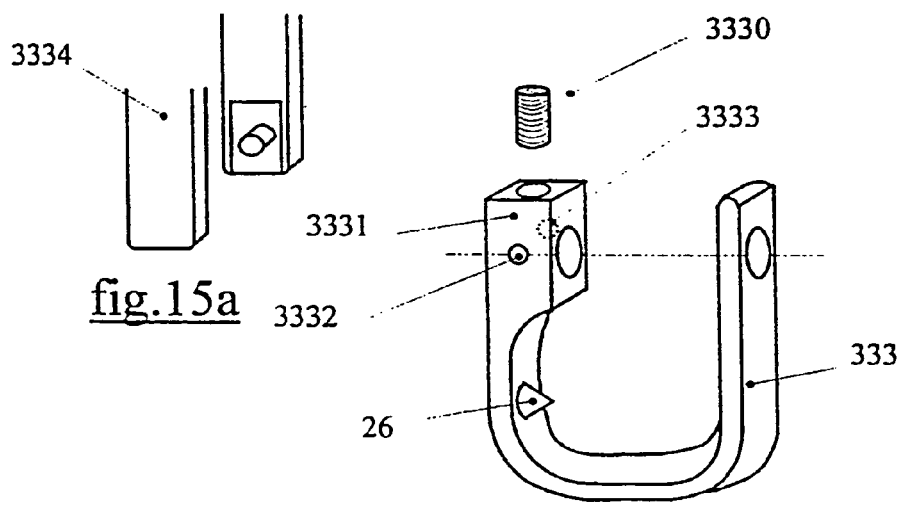
fig.15a
fig.15b

DISTRACTION DEVICE FOR THE BONES OF CHILDREN

FIELD OF THE INVENTION

The invention relates to a tensioning device that is placed between the ribs of a child whose growth is incomplete and who has deformations or malformations particularly of the trunk. In such a case, surgeons who specialize in this type of intervention call it: distraction device. It permits correcting also congenital malformations such as those that appear in the course of growth, without hindering or blocking the latter; it is in particular thanks to the means used that this invention can solve the problem, until now unsolved.

PRIOR ART

The first treatments of scoliosis were based on movements of the vertebral column. Y Cotrel perfected this technique by employing in 1892 a traction and elongation device for the spinal column. This traction of the spinal column was very painful. For the most serious cases, it was followed by a plaster cast on the chest to seek to preserve as much as possible the correction that had been carried out. Most often, the doctor would prescribe the wearing of a corset which more or less maintained the spinal column. For the most serious deformations, the results were far from being satisfactory. The spinal column did not straighten sufficiently and the wearing of the corset was annoying. Despite all these drawbacks, this method is still used for treatment of scoliosis of young children.

About 30 years ago, Harrington was the first to implant in the back of a patient a rod with two hooks fixed at their ends to the bones to try to straighten the spinal column. The spinal column was straightened, but 6 months later, once the graft had set, the vertebrae formed a bony mass limiting the mobility of the untreated vertebrae.

The often great distance between the two hooks made it necessary that the rod connecting them be subjected to strong forces, giving rise to breaking of the rods and thus requiring the surgeon to intervene. An immobilization of 6 months in a plastic cast was often necessary. Moreover, the correction was effected only in a single plane. The sagittal balance (lumbar lordosis and anatomical thoraxic cyphosis) were not maintained, and postoperative problems followed for the patient.

Yves Cotrel in 1988 produced a device for supporting the vertebrae of the spinal column. He multiplied the contacts with the vertebrae so that instead of two hooks for one framework, there was a system which could have up to two hooks or two screws per vertebra, which permits reducing the forces on the rod connecting the implants. Moreover, he used a technique of three-dimensional straightening of the spinal column. The spinal column is not only straightened in the frontal plane but the lumbar lordosis and the thoraxic cyphosis are also restored. The rods and hooks are solidly fixed to each other ensuring the holding of the spinal column during the time the bony graft sets up. The patient can return to normal activity sometime after the procedure. At the end of six months, the spinal column is in principle fused, the material remains in place. It is also this type of intervention that is carried out most often nowadays. The column is corrected, it is true, but the affected vertebrae are blocked. The patient, to recover mobility in the trunk, is obliged to compensate with the intervertebral disks free from any material.

The great drawback of this procedure is thus that it definitively fixes the spinal column; the growth of the fused vertebrae is blocked. If the surgeon operates on a child whose growth is not complete, he will block the growth of the vertebrae behind, by leaving the frontal growth free, which gives rise to the development of a deformation in the form of a twist. This is the "crankshaft" phenomenon noted by Professor Dubousset.

This is why the fixing of the vertebrae is not to be performed in young children. In this case, there is used only the treatments by corsets or plastic casts to limit and slow the development of the deformation. As soon as the child will have grown sufficiently, the surgeon can secure the spine by the technique described above, which cannot in any way be adapted to the problems of growth. For certain children having congenital malformations, the fact of achieving adulthood is not possible and the surgeons are obliged to fuse several vertebrae to permit a minimum respiratory capacity.

The present invention which will now be described in three illustrative and non-limiting embodiments, will permit solving these problems that confront all children whose growth is not complete.

DESCRIPTION

The present distraction device is comprised of devices for hooking onto the suitable bones, for example to the ribs, and devices for adjusting the interval between the two hooking devices.

The hooking devices are independent of the original distance of the ribs to be covered: for example, one end of the hooking device can be hooked to one given rib and to another rib which is not necessarily the nearest one.

The adjustment means permit both adjusting and correcting the deformation which will develop with growth by checking this movement on the assembly of the distraction device, whose adjustment can easily be periodically modified.

This invention will be described in connection with three preferred embodiments which permit adapting on a case by case basis to the problem arising, by illustrating with the drawings examples of embodiment, FIG. 1 shows an assembly view of a first type of distraction device for the bones FIG. 2 is a top plan view of the assembly of the distraction device (first embodiment)

FIG. 9 shows a top plan view of the distraction device in its third embodiment,

Figure 13:
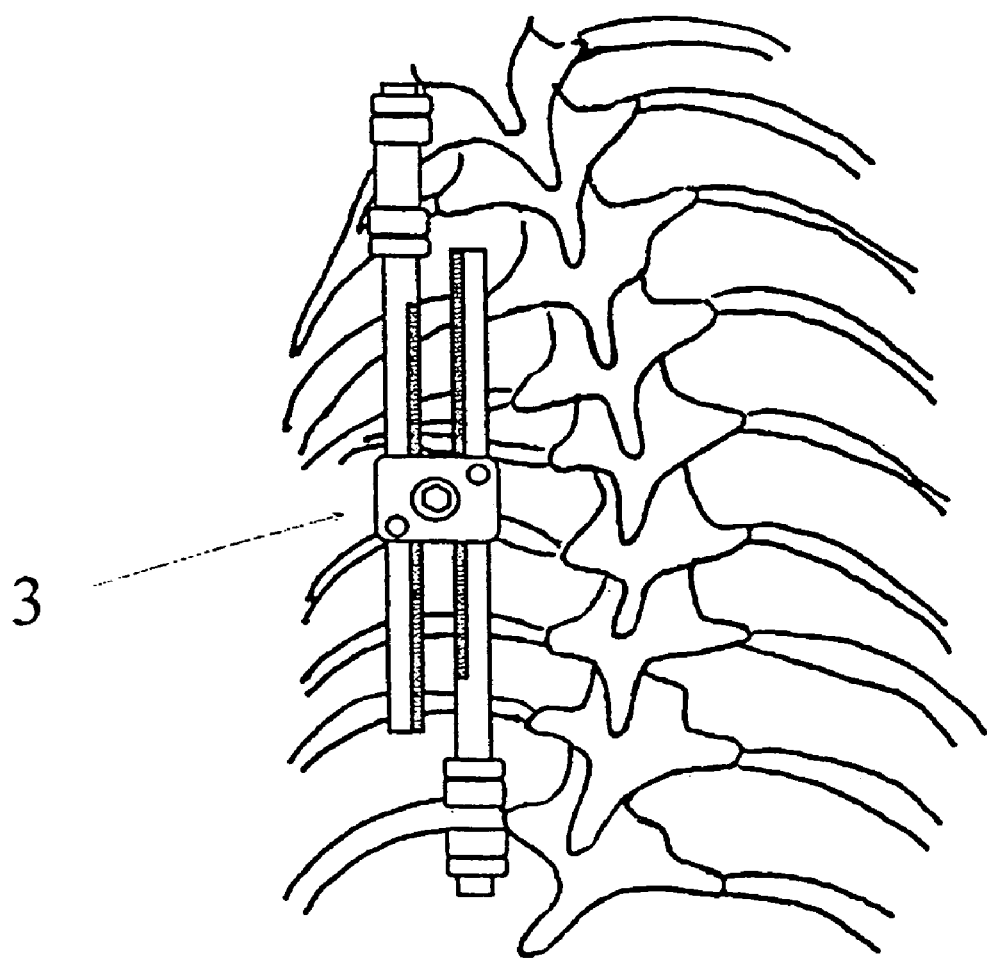

FIGS. 10, 11 and 12 show details of the adjustment device of the distraction device seen from above, an example of mini-tool for adjustment, and a perspective view, FIG. 13 shows one of the distraction devices in place on the skeleton, FIG. 14 shows a vertical cross-sectional view of a new distraction device of the 3rd embodiment comprising at the ends of the bendable or deformable rods supporting stirrups at their ends, FIGS. 15a and 15b show a perspective view of a hooking comprising at one end a tightening screw disposed in an enlargement and the detail of the jaws of a gripping member.

A first embodiment is a distraction device 1 which comprises: an adjustment device 100 and a device for hooking to the bones.

The adjustment device 100 comprises: at least one screw-threaded rod 11 with at its center an adjustment means 12 which can be of one piece with the rods or engaged on these rods, permitting the adjustment of the distraction device 1. It has at its center a small central hole 120 for receiving a mini-tool 121, the shape of the hole being suitable to the tool such that it will permit displacement of the hooking device located on the bones and thereby adjust their spacing.

The screw-threaded rod 11 has in its two symmetrical portions reversed screw threads (left and right) on which are screwed two hooking devices for the bones 13 and 14.

These hooking devices 13 and 14 can be in a first embodiment two plates 131 and 132 for hooking to the bones by matching perfectly its form, they are provided with securement screws 133 and 134 offset with respect to the axis of the adjustment device.

When the child grows, a small incision is made exactly over the place of the hole 120 corresponding to the passage of the mini-tool, and the hooking devices 13 and 14 are adjusted, thereby avoiding any inconvenience as described in the case of inventions of the prior art which are not capable of following growth.

In a second embodiment, which is a modification of the first embodiment, the adjusting device 200 comprises:

a central sleeve 27 permitting the desired spacing between two bones. This central adjustment sleeve 27 and at least one mini-hole 220 or several mini-holes 220 offset to permit easier access for example of a mini-rod which can be inserted to adjust at the desired location the distance between the two bones. Each screw-threaded rod with reversed pitch enters the central means which comprises on each end a suitable screw thread and on its external shape flats or cutoffs permitting turning it by external pressure of a mini-key adapted to its shape. This permits the surgeon to intervene for adjusting the device.

This adjustment device 200 is integrated very easily into the body by protecting the active portions 233 or 234 (screw-threaded rods 21a or 21b) from the tissues and from the surrounding skeleton.

Figure 1:
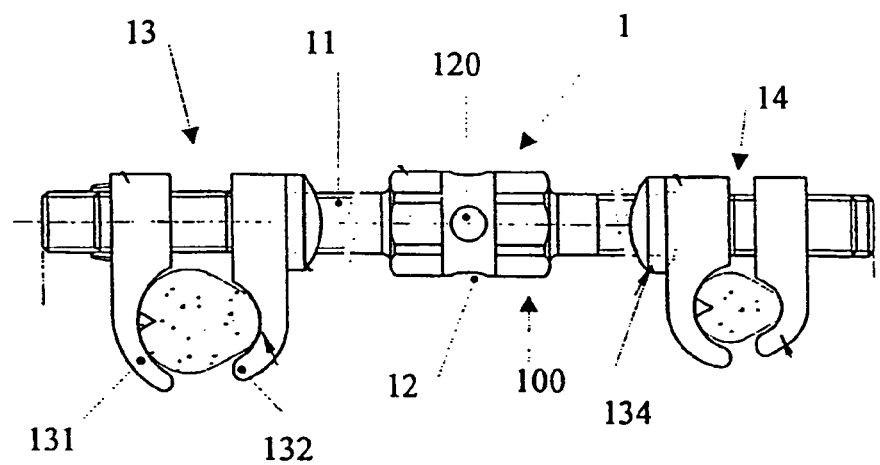
Figure 2:
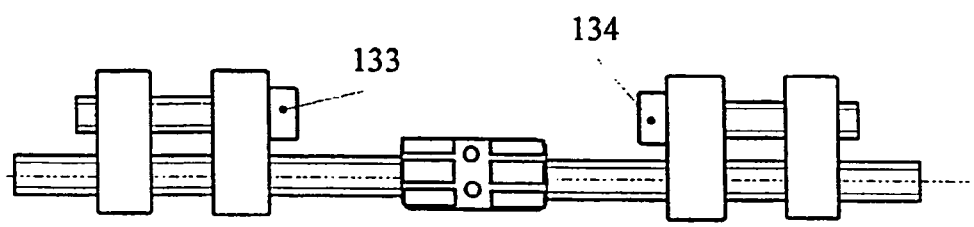
Figures 3, 4, 5:
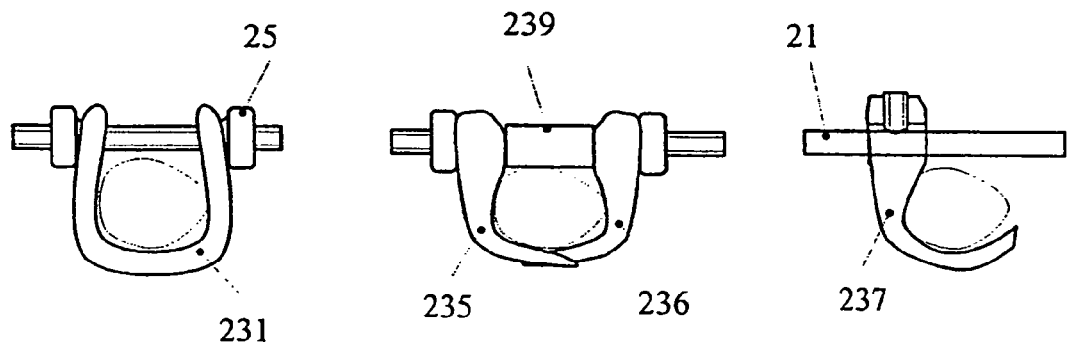
FIGS. 3, 4 and 5 show three examples of means for hooking to the bones.
Figure 6:
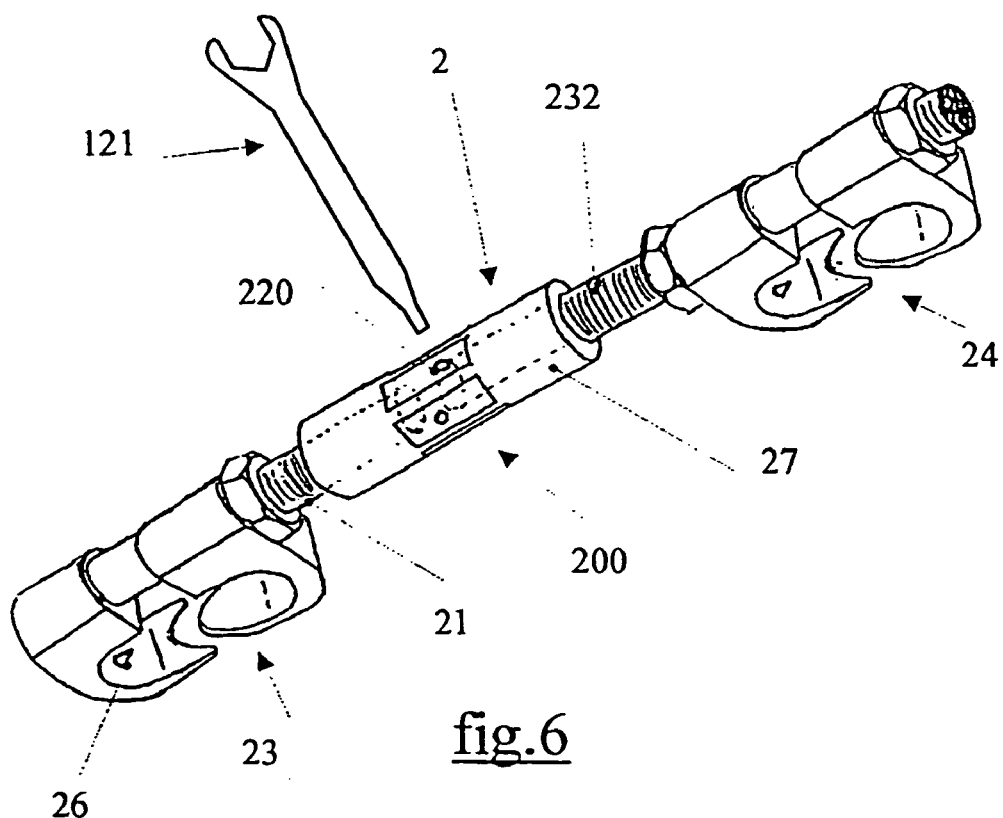
FIG. 6 shows an assembly view of a modified embodiment of the device with its mini-tool (the second embodiment)
Figure 7:
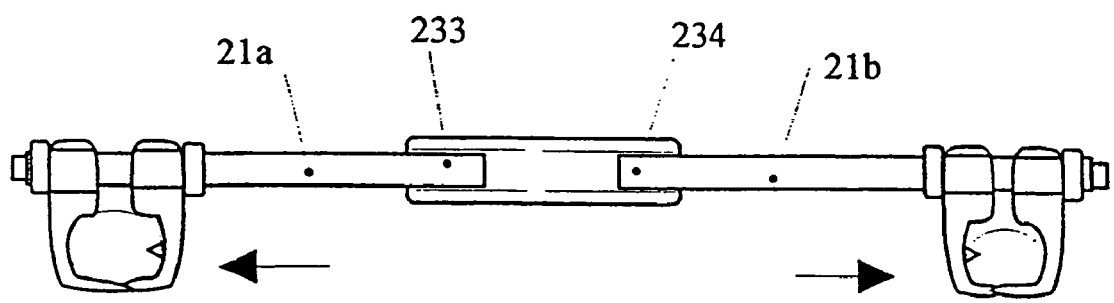
FIG. 7 shows a cross-sectional view (of the second embodiment)
Figure 8:
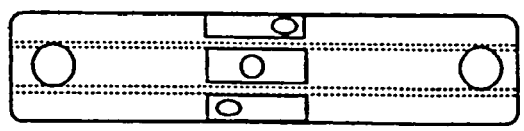
FIG. 8 shows the adjustment means of the assembly of the distraction device (second embodiment)

The hooking device is in this case constituted for example by hooking means 23 and 24 which can be:

either: stirrups 231 which screw onto screw-threaded rods 21a or 21b with blocking by a nut 25 or: hooks 235 and 236 formed of two male and female portions mating to the shape of the bone or again a sliding hook 237 on the rod 21 which can be smooth, screw-threaded or milled and on which the hook will be fixed by a screw 2370 embedded in an enlargement forming part of the hook 237 (FIG. 5).

In addition to these hooking means (FIGS. 3, 4 and 5), the hooks or stirrups can have a point 26 (FIG. 15) which will pierce the bone so as better to immobilize it. Moreover, it is preferable to place a tubular crosspiece 329 between the hooks 235 and 236 so as to avoid any sliding of the bone by opening of the hooks from gripping, thereby permitting obtaining a very effective encircling of the bone.

The third embodiment of the distraction device 3 comprises:

An adjustment device 300 which comprises a central means 31 itself comprised by a small frame 310 (smaller than the dimension for example of a domino), in which freely turns on an axle a small wheel 311 which can be toothed, centered on said frame 310 and having at one of the ends of its axle a means 312 for rotating it with the desired amplitude. This means can be a hole permitting the engagement of a male key with six flats 321, or any other equivalent means, its only requirement being to be received without projection in said frame 310.

In this frame will be positioned on each rib of the wheel 311 two rods 35 and 36 which will be moved in translation as required thanks to the adjustment means 31 located on the frame 310 and accessible by a mini-tool 321. The two rods 35 and 36 can have a channeled portion followed by a screw-threaded portion which permits very easily engaging symmetrically the screw-threaded portions to the channeled portion, permitting thereafter the systematic engagement in the wheel 311. Before proceeding to the final adjustment, upon engagement of the rods, the mini-tool can be engaged in the adjustment device 31 to start the distraction which will take place then in a semi-automatic manner and will proceed by using the mini-tool to perfect the adjustment. This operation is of course after having hooked the previously described hooking means to the bones. In this embodiment, the blocking of the adjustment device 31 takes part by tightening the two screws 341 and 342 located on the frame 310. On the other hand, a small cover constituted by a vertical plate 330 located between the two rods, or a plate that is pierced to let them pass, closes the frame by avoiding introduction particularly of tissue into the frame, without interfering with the movement of the rods 35 and 36 in translation by the toothed wheel operated by the surgeon.

In the third embodiment of the distraction device 3, it is also possible to correct a deformation that can develop in a three-dimensional space.

To obtain such a result, there are emplaced preferably within the distraction device 3 a new hooking means of the stirrup type 333 rods 35 and 36 with bendable or deformable ends 38 and 39, this new stirrup 333 has a tightening screw 3330 disposed in an enlargement 3331 forming a portion of the body of the stirrup, as well as two small holes 3332 and 3333 permitting access to a specific gripper 3334 whose jaws can be positioned in the holes to be able to raise the rib or the bone and to bring the rod 35 or 36 to be threaded on said hooking means 333. This manipulation is made possible the ends of the rods 38 and 39 are deformable as needed. Once the distraction device 3 is emplaced, the screws 3330 are tightened, the hooks are brought together or spaced apart by the desired distance and the central adjustment means 300 is tightened by the adjustment screws 341 and 342. This manipulation is without risk to the child, because the bending to measure of the ends of the rods 38 and 39 permits pure translatory movement, rendered impossible with rods that are straight and rigid over all the length.

Moreover, there is no possible error of manipulation because the tightening screw 3330 disposed in the enlargement 3331 cannot be lost, which thus permits, thanks to the means previously described, correcting a three-dimensional deformation without risk of error.

Thanks to the means previously described in the preferred embodiment No. 3, it is possible to proceed to a mechanical mounting on the bones or the ribs which can be carried out easily in the following way:

we start by positioning the stirrup 333 with its rod 35 about the bone without gripping it with the screw 3330, which permits rotation of the assembly about the bone which thereby permits threading the two rods 35 and 36 with their adjustment means 31, which are caused to slide to the ends 38 and 39.

With the help of the adjustment means 31, the second rod (for example 36) is brought into the hooking means 333 pre-positioned on the second rib which is not necessarily the nearest one; this emplacement is possible thanks only to the ends 38 and 39 which can be bent to measure, of the rods 35 and 36, which permit reaching a position in practically all difficult cases encountered. Once the adjustments have been determined, it remains only to carry out the tightening of the various means of the distraction device 3.

The three embodiments of the distraction device 1, 2, 3 thus permit, thanks to the means for using them, previously described, to straighten the bones of a child, without thereby finally blocking it, because straightening the skeleton of a child, without thereby finally blocking it, because it suffices to carry out a small intervention to have access easily to the distraction device, which permits following the development of this skeleton by correcting the deformations whilst permitting the child to grow. In embodiments 2 and 3, the structure of the hooking devices is perfectly interchangeable, and not specific except for the first embodiment. The third embodiment is distinguished however the most from the prior art.

Finally, all the devices which are used in any embodiment, comprise adjustment or hooking means that can be adapted to any shape of bones; they will be produced of materials that are biocompatible with the human body. As is known at present, the preference is toward unoxidizable metals: stainless steel, titanium alloys or other metals of high strength, insensitive to corrosion by the human body; composite materials of high strength and biologically compatible can also be envisaged. Given their small size, all these means can be assembled in "assembly kits"; these kits being present in chests used during an operation. All these new devices give to this invention a great advance as to technical devices already used for the care of malformations which will be able to be treated without impeding growth, with simple devices.

What is claimed is:

1. Distraction device (3) permitting controlling development of deformation of a trunk of a child in the course of the child's growth growth, the device easily implantable in the child's body due to small size, the device comprising:
   two rods (35, 36) mounted on a central adjustment means (300) provided with a small hole (312) for the engagement of a small tool (321) adapted to adjust the difference which separates means for hooking to the bones (231, 235, 236 or 239, 333), said device being adapted to be blocked in a predetermined position by tightening of two screws (341) and (342) located on the adjustment means (300).

2. Distraction device (3) according to claim 1, characterized in that it comprises two rods (35 and 36) comprised of two portions:
   a first portion permitting engagement of said rods in a small frame (310) and fixing the hooking means (231, 235, 236, 239, 333); and
   a second portion of said rods including a channel permitting systematic engagement in a toothed wheel (311) disposed in a small frame (310) thereby permitting opposite movement of the rods.

3. Distraction device according to claim 2, characterized in that said hooking means to the bones (231, 235, 236, 333) are essentially in the shape of a stirrup having a point (26) which pierces the bone so as better to immobilize it, and in that said stirrups can be fixed preferably by screws.

4. Distraction device (3) according to claim 3 characterized in that the stirrup comprises securement and adjustment and tightening means to permit easy mechanical emplacement in the body of the child because of an untightened initial positioning of a first hooking means (333) on a first bone which permits rotation about this first bone, thereby facilitating the threading and engagement of the rods by raising the assembly to the desired height relative to a point of rotation, then by bringing to the level of the second identical hooking (333) disposed on another bone in a predetermined position with tightening of all the screws of the distraction device (3) that it is desired to emplace.

5. Distraction device (3) according to claim 2 characterized in that its frame (310) comprises a small cover (300) constituted by a plate between the two rods or a plate that is pierced to let the rods slide closing said frame, thereby avoiding the introduction particularly of tissue into the frame, whilst leaving free the movement of said rods.

6. Distraction device (3) according to claim 1 characterized in that the hooking means to the bones comprise hooks (235) and (236) received within each other and a tubular crosspiece (239) located between two hooks, said device being blocked by at least one nut (25) or by a screw included in a hook, thereby forming a rigid and effective encircling of the bones.

7. Distraction device (3) according to claim 1 characterized in that it comprises:
   at least one hooking means of a stirrup configuration (333); and
   rods (35 and 36) with bendable or deformable ends (38) and (39) permitting correcting deformation in a three-dimensional space.

8. Distraction device (3) according to claim 7 characterized in that its stirrup (333) has holes (3332 and 3333) for gripping, provided for a specific gripper (3334) whose jaws are positioned in said holes to raise the bones and the bendable ends (38 and 39) to thread the bendable ends on the hooking means.

9. Distraction device (3) according to claim 8 characterized in that adjustment means is configured to provide translation of the rods and to allow the bending of the ends (38 and 39) of the rods, the bending of the rods carried out to measurement to permit movement of distraction in pure translation without the risk of aggression to the body of the child which would necessarily arise from the use of straight rods rigid over all their length.

10. Distraction device (3) according to claim 8 characterized in that its hooking means (333) has a tightening screw (3330) disposed in an enlargement (3331) which is hence proof against loss and is pre-positioned, during the emplacement of the distraction device (3) and permitting, once this positioning has taken place, fixing, by tightening said screw, the hooking means to the rod ends (38) and (39).

11. Distraction device (3) for controlling development of deformation of a trunk of a child in the course of the child's growth, comprising:
   a central adjustment device (300);
   two rods (35, 36) mounted on said adjustment device;
   hooking parts (231, 235, 236 or 239, 333) attached to said two rods for hooking to bones of the child, a distance separating said hooking parts being adjustable via operation of said adjustment device;
   an adjustment hole (312) within said adjustment device for engagement of a removable adjustment tool (321)

adapted to operate said adjustment device to adjust a difference of the distance separating said hooking parts; and two screws (341, 342) located on said adjustment device, said two screws tightenable to block said two rods and said two hooking parts in a predetermined position fixing the distance separating said hooking parts, wherein, the device permits controlling the development of deformation of the trunk of the child in the course of the child's growth growth, and the device configured for implantation in the child's body.

12. Distraction device (3) according to claim 11, wherein, each of said two rods (35, 36) comprise a first portion and a second portion, said adjustment device comprises a frame (310) and a toothed wheel (311) disposed in said frame, said first portion permits engagement of said two rods in said frame and fixing said hooking parts, and said second portion comprises a channel systematically engaged in said toothed wheel to provide opposite movement of said two rods.

13. Distraction device according to claim 12, wherein, said hooking parts are essentially in the shape of a stirrup having a point (26) which pierces the bone to immobilize the bone, and said stirrups comprise fixing screws.

14. Distraction device (3) according to claim 13, wherein, said stirrup comprises first and second identical hooking means with securement and adjustment and tightening parts permitting mechanical emplacement in the body of the child, in an untightened initial positioning of the first hooking means (333) on a first bone, the first hooking means being rotatable about the first bone to facilitating threading and engagement of the rods by raising the assembly to a desired height relative to a point of rotation and a level of the second hooking means (333) disposed on another bone.

15. Distraction device (3) according to claim 12, wherein, said frame (310) comprises a cover constituted by one of i) a plate between said two rods and ii) a plate that is pierced to let said two rods slide closing said frame, said cover blocking introduction of tissue into the frame, whilst leaving free the movement of said rods.

16. Distraction device (3) according to claim 11, wherein, said hooking parts comprise two hooks (235, 236) received within each other and a tubular crosspiece (239) located between said two hooks, said hooking parts are blocked by at least one of a nut (25) and a screw included in a hook to form a rigid and effective encircling of the bones.

17. Distraction device (3) according to claim 11, wherein, at least one of said hooking parts is a stirrup (333), and said rods (35, 36) comprise bendable ends (38, 39) permitting correcting deformation in a three-dimensional space.

18. Distraction device (3) according to claim 17, wherein, said stirrup (333) comprises gripping holes (3332, 3333) for gripping, and a gripper (3334) with jaws positioned in said gripping holes, and the gripper is configured to adjust a position of an engaged bone to allow the bendable ends to be threaded on the hooking part.

19. Distraction device (3) according to claim 18, wherein, said adjustment means is configured to bend the bendable ends in pure translation.

20. Distraction device (3) according to claim 18, wherein, said stirrup part (333) further comprises a tightening screw (3330) disposed in an enlargement (3331), said tightening screw, when tightened, fixing said hooking part to said bendable ends.

* * * * *